United States Patent [19]

Bradshaw

[11] Patent Number: 4,468,966

[45] Date of Patent: Sep. 4, 1984

[54] RAILROAD TRACK INSPECTION CAR

[75] Inventor: Bruce W. Bradshaw, Ludington, Mich.

[73] Assignee: Jackson Jordan; Inc., Ludington, Mich.

[21] Appl. No.: 413,615

[22] Filed: Sep. 1, 1982

[51] Int. Cl.³ .......................................... G01N 29/04
[52] U.S. Cl. .................................. 73/636; 105/215 C
[58] Field of Search ..................... 73/636, 634, 635; 105/215 C

[56] References Cited

U.S. PATENT DOCUMENTS

| | | | |
|---|---|---|---|
| 2,992,553 | 7/1961 | Joy | 73/636 |
| 3,028,753 | 4/1962 | Joy | 73/636 |
| 4,044,594 | 8/1977 | Owens | 73/636 X |
| 4,103,622 | 8/1978 | Theurer | 105/215 C X |
| 4,381,713 | 5/1983 | Cripe | 105/215 C |

Primary Examiner—Stephen A. Kreitman
Assistant Examiner—Vincent P. Kovalick
Attorney, Agent, or Firm—Leydig, Voit, Osann, Mayer & Holt, Ltd.

[57] ABSTRACT

A track inspection car supported on railroad track by flanged wheels mounted on a truck, and having means for engaging a tractor-truck at one end and wheels with highway tires at the other. The wheels are relatively vertically displaceable by selectively inflating pneumatic springs for converting the car from on-track operation to an off-track trailer-truck configuration. A pair of ultrasonic sensor probes are mounted on the wheel truck coupled to a computer in the car. The car also includes an on-track driving motor, a driver station, a computer operators station, an observer's station, and a water supply for creating a fluid acoustical coupling between the sensors and the rails.

4 Claims, 3 Drawing Figures

RAILROAD TRACK INSPECTION CAR

This invention relates generally to railroad track inspection cars and more particularly concerns a car suited for ultrasonic testing of track rails.

Vehicles adapted for traveling both on railroad track and highways are well known. Automobiles and light trucks so adapted are often called "hi-rail" vehicles. Some specialized track working machines such as the smaller ballast tampers have also been so adapted, either as complete highway vehicles as shown in the U.S. Pat. to Anderson et al. No. 3,494,300, or as the trailer type of vehicle in a tractor-trailer combinations, as shown in U.S. Pat. to Theurer No. 4,103,622.

Hi-rail vehicles have been used as track inspection cars capable of being driven down the track with sensors recording or displaying the condition of the rails. Although most rail testing of track in place in the United States utilizes electromagnetic sensing, ultrasonic sensing has the potential for greater precision suitable for being interpreted with modern data acquisition and display systems, i.e., computers. Ultrasonic sensing does place demands on the carrying equipment. The probe itself is normally placed firmly against the rail, and it is therefore desirable to load the track so that rail joints are not vertically discontinuous which could jar or damage the probe. However, large heavy inspection cars are usually track-bound and hence present traffic problems and difficulties in transferring a car between railroads. Lighter vehicles having off-track mobility like hi-rail trucks do not have the weight to effectively load the track.

Accordingly, it is the aim of the invention to provide a heavy inspection car for sensing track that also has off-track mobility, such mobility being as a tractor-truck drawn highway trailer.

Another object of the invention is to provide a car of the foregoing type that supports a sensor like an ultrasonic probe in stable orientation relative to the track, and which facilitates both computer associated and visual monitoring of the track.

A further object is to provide a car as characterized above that can be simply converted between a heavy, self-propelled inspection car and an off-track vehicle in the form of a highway trailer and which, in either traveling mode, has good riding qualities.

Other objects and advantages of the invention will become apparent upon reading the following detailed description and upon reference to the drawings, in which.

While the invention will be described in connection with a preferred embodiment, it will be understood that I do not intend to limit the invention to that embodiment. On the contrary, I intend to cover all alternatives, modifications and equivalents as may be included within the spirit and scope of the invention as defined by the appended claims.

Figure 1:
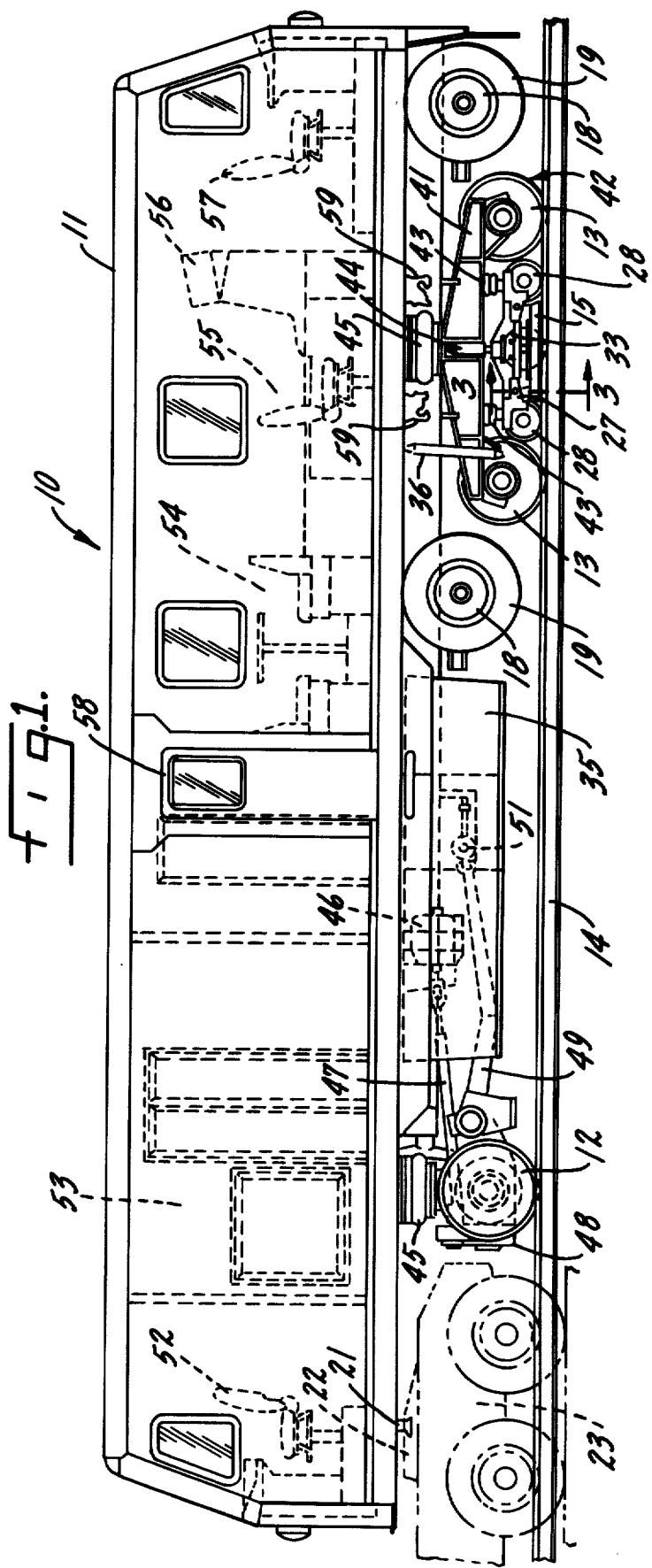
FIG. 1 is a side elevation of a car embodying the invention.
Figure 2:
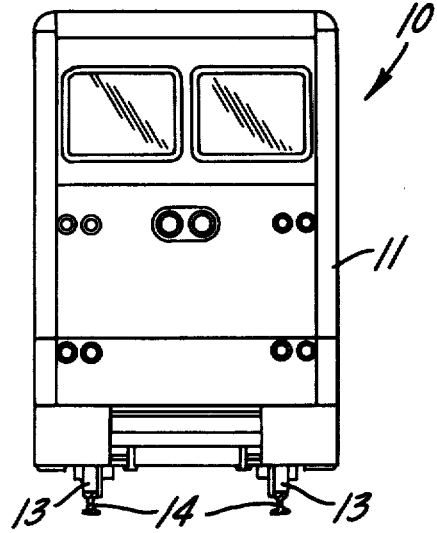
FIG. 2 is an end elevation of the car of the FIG. 1.

Turning now to FIG. 1, there is shown an inspection car 10 embodying the invention and having a body 11 and flanged wheels 12 and 13 configured to ride the rails 14 of railroad track under its own power. The sensor devices utilized by the car 10 are a pair of ultrasound probe shoes 15 that, when the car 10 is working, ride respectively on the top or ball 16 of each rail 14. As will be familiar to those skilled in this art, the probe shoes are blocks of rugged plastic encapsulating a number of piezo-electric crystal probes which send ultrasonic acoustic energy into the rails and receive reflected signals whose timing reveals information about the internal integrity of the rails. The forward, working direction of movement of the car 10 along the track is to the left in FIG. 1.

To provide off-track mobility for the car 10, wheels 18 carrying highway tires 19 are mounted near the rear of the car 10 to support that end, and the front end of the car is configured and provide with a kingpin 21 to mate with the fifth wheel 22 of a conventional tractor-truck 23 partially shown in dashed lines. Engaging the front end of the car with a tractor like the tractor-truck 23, and varying the relative vertical displacement of the flanged wheels 12, 13 and the highway tired wheels 18—so that the flanged wheels are raised and the tired wheels are lowered—allows the car 10 to be towed off-track as a highway trailer.

Figure 3:
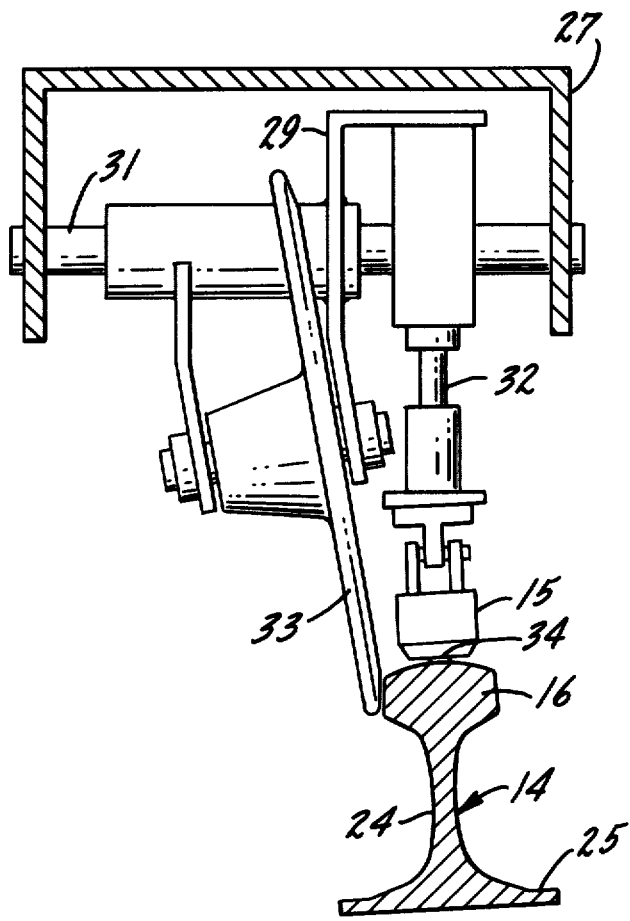
FIG. 3 is a fragmentary section taken approximately along the line 3—3 of FIG. 1.

As best seen in FIG. 3, the probe shoes 15 must be held in closely established relationship to the underlying rail 14 in order to perform their intended function. Several of the crystal probes in each shoe 15 direct waves through the web 24 of the underlying rail 14 to the web base 25, and hence the positioning and angle of the probe shoe on the rail ball 16 is rather critical. In the illustrated embodiment, each probe shoe 15 is carried on an elongated support 27 having rollers 28 adapted to ride on the underlying rail 14. A carrier 29 is mounted on slide shafts 31 fixed on the support 27 so that the carrier 29 can move transversely of the rail 14. The opposite ends of the probe shoes are pivoted to rods 32 which are mounted for vertical movement on the carrier 29.

The lateral position of the shoe 15 is fixed by a contact wheel 33 journaled on the carrier and riding on the inside of the rail head 16. Pneumatic actuators, not shown, bias the carrier 29 and hold the contact wheel 33 against the rail, and also bias the rods 32 down to press the probe shoe 15 firmly against the rail 14. As is conventional, a film of water 34 is created between the probe shoe 15 and the rail head 16 so as to provide good acoustic coupling between the crystal probes and the body of the rail. For this purpose, the car 10 includes a large water tank 35 from which, when the car is operating, a stream of water is directed through a hose 36 onto each rail 14 just ahead of the probe shoes 15.

In accordance with the invention, the probe shoe sensors and their associated positioning structures are mounted respectively on the side frames 41 of a railroad truck 42 journaling the four wheels 13. In this way, the weight of the rear of the car 10 is transmitted through the truck 42 to the track just fore and aft of the sensors, thus loading the track and tending to align adjacent rail ends. Also, the four-wheeled truck 42 with rigid side frames 41 forms a kind of truss solidly held on the track and providing a steady frame to hold the sensor shoes 15 in fixed relationship to the track rails 14. In the illustrated embodiment, the sensor supports 27 are held on the truck side frames 41 by heavy resilient connections 43, and an actuator 44 is provided to lift the supports 27, and thus the sensor shoes 15 clear of the track for high speed travel of the car 10.

To provide for vertical adjustment, and also good riding qualities, all of the wheels 12, 13, 18 are secured to the car body 11 through pairs of selectively inflatable pneumatic springs 45 in a suspension system of the kind marketed by the Bi-Modal Corporation and disclosed in U.S. Pat. to Brown et al. No. 4,202,277 on convertible Rail-Highway Semi-Trailer, issued May 13, 1980. By inflating the pairs of springs 45 for the axles of the wheels 12, 18, or for the truck 42, the wheels are shifted on the order of 7" from the car body, and the resulting air suspension gives the car good riding qualities on both track and highway.

The wheels 12 are the track drive wheels, and power is supplied from a hydraulic motor 46 through a drive shaft 47 and an axle gear box 48. The springs 45 supporting the axle gear box 48 are pneumatically interconnected, and a long tongue 49 pivoted for vertical movement at 51 on the car body 11 holds the wheels 12 against turning movement about a vertical axis while permitting limiting side-to-side movement relative to the body 11. The wheels 12 are thus floatingly mounted on the body 11, and forces are not imposed from the wheels 12 through the body 11 to the sensor carrying truck 42.

In the illustrating car 10, the body 11 encloses a driver's station 52, a diesel engine-generator compartment 53 providing power for the motor 46 as well as auxiliary power and compressed air, a crew utility area 54, a computer station 55 with a computer 56 coupled to the ultrasonic probes, and an observer's station 57. Access to the car body 11 is through a door 58.

To securely hold the retracted wheels 12, 13 or 18 up against the car body, latches like latches 59 shown for the truck 42 are provided for each wheel set.

Operation of the car 10 will be apparent from the foregoing description. With the wheels 18 down and the wheels 12, 13 up, the car may be towed to a desired track location by a tractor-truck 23 in the manner of a conventional truck-trailer combination. Upon reaching the desired track, the car 10 is pulled astraddle the track and the pneumatic springs 45 are inflated to lower the wheels 12 and the truck 42 onto the rails 14. The wheels 18 can then be raised by deflating their pneumatic springs and the wheels latched into position as illustrated. With the trailer-truck 23 disconnected, the car 10 can proceed under its own power at relatively high speed to the track that is to be tested. At this point, the actuator 44 is utilized to lower the ultrasound probe shoes 15 into firm contact with the track, and the testing can begin. The weight of the heavy car 10 is transmitted through the truck 42 to load the track so as to minimize variations in track height at rail joints which could damage the probe shoes or jar them from the desired intimate contact with the rail heads. Upon completion of the desired track testing, the car 10 can be easily converted back to its highway trailer configuration for highway movement to the next job site.

I claim as my invention:

1. A rail inspection car comprising, in combination, a body, a two-axle, four-flanged wheel, railroad truck having side frames supporting said body on track at one end of the body, a track sensor mounted on one of said frames in established relationship to the underlying rail, a pair of flanged wheels floatingly mounted on said body for supporting the other end of said body on said track, means at one end of said body for coupling the body to a tractor-truck, wheels carrying highway tires mounted near the body end not having said coupling means, and means for varying the relative vertical displacement of said flanged wheels and said highway tired wheels on said body for converting said car from an on-track vehicle to an off-track trailer.

2. The combination of claim 1 in which said body has a driver's station at one end and an observer's station at the opposite end, and the combination including a self-propelling motor in said body coupled to said pair of flanged wheels for driving the car on-track.

3. The combination of claim 1 in which said track sensor is an ultrasonic shoe probe for riding on the underlying rail, and the combination including a computer in said body coupled to said probe for receiving, interpreting and displaying signals from the probe, a water tank on said body, and means for feeding a stream of water from said tank to create a water film between said probe and the underlying rail.

4. The combination of claim 1 in which said means for varying the vertical displacement of said wheels includes selectively inflatable pneumatic springs.

* * * * *